(12) United States Patent
Gambogi et al.

(10) Patent No.: US 6,464,963 B1
(45) Date of Patent: *Oct. 15, 2002

(54) DESENSITIZING DENTIFRICE CONTAINING POTASSIUM AND TIN SALTS

(75) Inventors: Robert J. Gambogi, Belle Mead; Steven W. Fisher, Middlesex; Edward A. Tavss, Kendall Park; Marilou T. Joziak, South River, all of NJ (US)

(73) Assignee: Colgate Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/065,267

(22) Filed: Apr. 23, 1998

(51) Int. Cl.$^7$ .............................. A61K 7/16; A61K 7/18
(52) U.S. Cl. ........................................... 424/52; 424/49
(58) Field of Search ...................... 424/49–88

(56) References Cited

U.S. PATENT DOCUMENTS

| | | | | |
|---|---|---|---|---|
| 2,839,448 A | * | 6/1958 | Hager et al. .................. | 167/93 |
| 3,105,013 A | * | 9/1963 | Saul et al. ..................... | 167/93 |
| 3,282,792 A | * | 11/1966 | Fiscella ........................ | 167/93 |
| 3,335,912 A | * | 8/1967 | Reeves ......................... | 222/94 |
| 3,337,412 A | * | 8/1967 | Elbreuer ....................... | 167/93 |
| 3,747,804 A | * | 7/1973 | Raaf et al. .................... | 222/94 |
| 3,863,006 A | | 1/1975 | Hodosh ........................ | 424/49 |
| 4,211,341 A | * | 7/1980 | Weyn .......................... | 222/94 |
| 4,267,167 A | * | 5/1981 | Weitzman et al. ............. | 424/52 |
| 4,374,823 A | * | 2/1983 | Harvey et al. ................. | 424/52 |
| 4,418,057 A | * | 11/1983 | Groat, I et al. ............... | 424/151 |
| 4,533,544 A | * | 8/1985 | Groat, II et al. .............. | 424/52 |
| 4,961,924 A | * | 10/1990 | Suhonen, I ................... | 424/52 |
| 5,017,363 A | * | 5/1991 | Suhonen, II .................. | 424/52 |
| 5,240,697 A | * | 8/1993 | Norfleet, I et al. ............ | 424/52 |
| 5,352,439 A | * | 10/1994 | Norfleet, II et al. ........... | 424/52 |
| 5,374,417 A | * | 12/1994 | Norfleet, III et al. .......... | 424/49 |
| 5,486,350 A | * | 1/1996 | Norfleet, IV et al. .......... | 424/49 |
| 5,487,906 A | * | 1/1996 | Dixit et al. .................... | 424/52 |
| 5,503,823 A | * | 4/1996 | Norfleet, V et al. ........... | 424/52 |
| 5,505,933 A | * | 4/1996 | Norfleet, VI et al. .......... | 424/52 |
| 5,571,501 A | * | 11/1996 | Toy .............................. | 424/49 |
| 5,578,293 A | * | 11/1996 | Prencipe et al. .............. | 424/49 |
| 5,674,474 A | * | 10/1997 | Fisher et al. .................. | 424/52 |
| 5,690,912 A | * | 11/1997 | Campbell, I et al. .......... | 424/52 |
| 5,693,314 A | * | 12/1997 | Campbell, II et al. ......... | 424/49 |
| 5,780,015 A | * | 7/1998 | Fisher .......................... | 424/52 |
| 5,843,409 A | * | 12/1998 | Campbell, III et al. ........ | 424/52 |
| 5,849,267 A | * | 12/1998 | Collins et al. ................. | 424/49 |
| 5,851,512 A | * | 12/1998 | Fischer ......................... | 424/49 |
| 6,180,089 B1 | * | 1/2001 | Gambogi et al. .............. | 424/52 |

FOREIGN PATENT DOCUMENTS

| | | | | |
|---|---|---|---|---|
| EP | 0696405 | | 2/1996 | ............ A61K/7/16 |
| WO | 9528911 | | 11/1995 | ............ A61K/7/18 |

* cited by examiner

Primary Examiner—Marianne C. Seidel
(74) Attorney, Agent, or Firm—Paul Shapiro

(57) ABSTRACT

A two component desensitizing dentifrice composition is disclosed which comprises a first dentifrice component containing a desensitizing potassium salt such as potassium nitrate and an alkali metal compound such as NaOH and a second dentifrice component containing a desensitizing stannous salt source such as stannous, the first and second dentifrice components being maintained separate from the other until dispensed for application to teeth.

15 Claims, 1 Drawing Sheet

DESENSITIZING DENTIFRICE CONTAINING POTASSIUM AND TIN SALTS

BACKGROUND OF THE INVENTION

1. Field of the Invention

The present invention relates to a desensitizing dentifrice composition which eliminates or reduces the discomfort and pain associated with dentinal hypersensitivity and more particularly to a two-component desensitizing dental composition containing tin salt and potassium salt desensitizing agents.

2. The Prior Art

Dentinal hypersensitivity is defined as acute, localized tooth pain in response to physical stimulation of the dentine surface as by thermal (hot or cold) osmotic, tactile combination of thermal, osmotic and tactile stimulation of the exposed dentin.

Exposure of the dentine, which is generally due to recession of the gums, or loss of enamel, frequently leads to hypersensitivity. The art has determined that dentine tubules open to the surface have a high correlation with dentine hypersensitivity, Abs, J. Clin. Periodontal. 14,280–4 (1987). Dentinal tubules lead from the pulp to the cementum. When the surface cementum of the tooth root is eroded, the dentinal tubules become exposed to the external environment. The exposed dentinal tubules provide a pathway for transmission of fluid flow to the pulpal nerves, the transmission induced by changes in temperature, pressure and ionic gradients. Tin salts such as $SnF_2$ have been indicated clinically to be efficacious in the reduction of dentinal hypersensitivity. This latter therapeutic effect is believed to be attributable, to a large degree, to the stannous ion ($Sn^{2+}$) component of the salt. $SnF_2$ is believed to be effective in desensitization by occlusion of exposed dentinal tubules wherein deposits of low solubility complexes of tin are formed on the surface of exposed dental tubules effectively blocking the openings. When hypersensitive teeth are treated with dentifrices containing tin salts such as $SnF_2$, tin deposits accumulate on the tooth surface with each treatment until complete, or virtually complete, coverage of the exposed dentine tubules occurs. By blocking the dentinal tubules external stimuli have a diminished effect, resulting in less pain.

It is also known to the art that potassium salts are effective in the treatment of dentinal hypersensitivity. For example, U.S. Pat. No. 3,863,006 discloses that toothpastes containing potassium salts such as potassium nitrate desensitize the teeth after tooth brushing for several weeks. It is believed by those skilled in the art that an elevation in the extracellular potassium concentration in the vicinity of pulpal nerves underlying sensitive dentin is responsible for the therapeutic desensitizing effect of topically applied oral products which contain potassium nitrate. Due to passive diffusion of potassium ion into and out of the open dentine tubules, repeated application of the active ingredient is necessary to build up the necessary concentration in the vicinity of the pulpal nerves.

Attempts to include mixtures of desensitizing agents such as $SnF_2$ and potassium salts such as potassium nitrate in a single desensitizing dental composition have been found to be of limited effect as a means for delivering efficacious amounts of both ingredients to the teeth. In the case of tin salts such as $SnF_2$, insoluble stannic salts and stannous compounds such as $Sn(OH)_2$ and $SnO_2$ are formed in the composition during storage, and the insoluble salt is ineffective in occluding the dentin surface to provide the desired desensitizing effect.

U.S. Pat. No. 5,693,314 discloses a two component desensitizing dental composition in which a first dentifrice component contains a desensitizing potassium salt and a second gel component contains a desensitizing stannous salt, the first and second components being maintained separate from each other until dispensed for application to teeth requiring relief from dentine hypersensitivity. It is believed that the improved pain relief obtained from the use of the combination of stannous and potassium salts is due in part to the gradual mineralization on the dentin surface which can either totally or partially occlude dentin tubules. Total occlusion will dramatically reduce fluid flow within the tubules which stimulates pain. Partial occlusion of the dentin tubules is believed to increase delivery of potassium ion inside the tooth because the inward diffusive flux is less dependent upon tubule radius than outward fluid flow (due to positive pulpal pressures). Therefore, this enhanced delivery of potassium should enhance relief.

Although the two component desensitizing dental composition of U.S. Pat. No. 5,693,314 is highly effective in the treatment of dentine hypersensitivity, efforts continue to further enhance the efficacy of this type of composition.

SUMMARY OF THE INVENTION

The present invention encompasses a dual component desensitizing dental composition in which the individual components are manufactured separately before use, the individual components when combined and applied to the teeth provide a composition which contains a desensitizing combination of a potassium salt and tin salt desensitizing agent whereby improved pain relief is attained.

The present invention is based upon the discovery that when a water soluble alkaline compound such as NaOH is included in the potassium salt containing dentifrice component at a concentration of about 0.5 to about 15% by weight, the combined composition exhibits improved effectiveness when applied to the teeth in obturating dentinal tubules with concomitant desensitization of teeth as compared to compositions in which the alkaline agent is absent.

DESCRIPTION OF THE PREFERRED EMBODIMENTS

Figure 1:
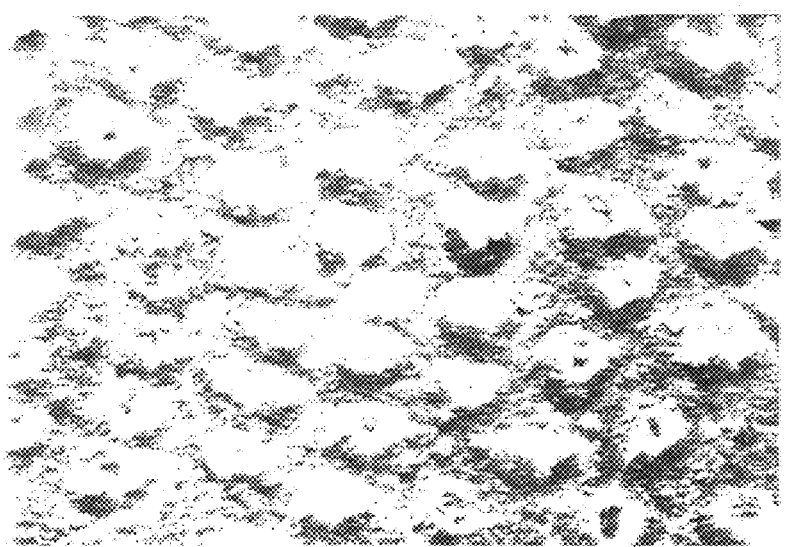
FIG. 1 is a scanning electron photomicrograph (SEM) (2,000×magnification) of a dentin disk surface treated with a combined dual component dentifrice containing both tin and potassium salts as well as an alkaline agent were present in accordance with the practice of the present invention.

To prepare the potassium salt containing desensitizing dentifrice component of the present invention, the potassium salt and the alkaline agent are generally incorporated in dentifrices which normally include a vehicle which contains water, humectant, surfactant and an abrasive. The pH of such dentifrice is in the alkaline range of about 8.0 to 11.0. It is critical to the practice of the present invention that the alkaline agent be present only in the potassium salt containing dentifrice component as stannous salts are not stable in alkaline environments.

Alkaline agents such as alkali metal compounds including sodium hydroxide, potassium hydroxide, sodium bicarbonate, sodium carbonate are incorporated in the potassium salt desensitizing component of the present invention in amounts in the range of about 0.5 to 15% by weight, preferably about 1.0 to about 8% by weight and most preferably at about 1.0 to abut 5.0% by weight of the potassium salt desensitizing component. Mixtures of the above alkali metal compounds may also be used.

The humectant used in the preparation of the potassium desensitizing salt dentifrice component is generally a mixture of humectants, such as glycerol, sorbitol and a polyethylene glycol of molecular weight in the range of 200–1000, but other mixtures of humectants and single humectants may also be employed. The humectant content is in the range about of 10% to about 80% by weight and preferably about 20 to about 50% by weight of the dentifrice component. The water content is in the range of about 10 to about 40% by weight.

The source of desensitizing potassium ion is generally a water soluble potassium salt including potassium nitrate, potassium citrate, potassium chloride, potassium bicarbonate and potassium oxalate with potassium nitrate being preferred. The potassium salt is generally incorporated in the dentifrice component containing alkaline compounds at a concentration of about 0.5 to about 20% by weight and preferably about 3 to about 15% by weight.

Inorganic thickeners may be included in the dentifrice component in which the desensitizing potassium salt is present as an ingredient and such thickeners include amorphous silicas such as Zeodent 165 available from Huber Corporation, and Sylox 15 from W. R. Grace.

Organic thickeners of natural and synthetic gums as colloids may also be incorporated in the dentifrice component of the present invention in which the potassium salt is present as an ingredient. Examples of such thickeners are carrageenan (Irish moss), xanthan gum, sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose.

The inorganic thickener may be incorporated in the potassium salt dentifrice component of the present invention at a concentration of about 0 to about 5% by weight and preferably about 1 to about 3% by weight. The organic thickener may be incorporated in the compositions of the present invention at a concentration of about 0.1 to about 3% by weight and preferably about 0.4 to about 1.5% by weight.

Surface active agents may be incorporated in the dentifrices in which a desensitizing potassium salt is included as an ingredient to provide foaming properties. The surface-active material is preferably anionic or nonionic in nature. Suitable examples of anionic surfactants are higher alkyl sulfates such as potassium or sodium lauryl sulfate which is preferred, higher fatty acid monoglyceride monosulfates, such as the salt of the monosulfated monoglyceride of hydrogenated coconut oil fatty acids, alkyl aryl sulfonates such as sodium dodecyl benzene sulfonate, higher fatty sulfoacetates, higher fatty acid esters of 1,2 dihydroxy propane sulfonate.

Examples of water soluble nonionic surfactants are condensation products of ethylene oxide with various hydrogen-containing compounds that are reactive therewith and have long hydrophobic chains (e.g., aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides and other fatty moieties, and with propylene oxide and polypropylene oxides (e.g., Pluronic® materials).

The surface active agent is generally present in the potassium salt dentifrice compositions of the present invention at a concentration of about 0.5 to about 10.0% by weight and preferably about 1.0 to about 5.0% by weight.

Abrasives may be incorporated in the desensitizing potassium salt containing dentifrice component of the present invention and preferred abrasives are siliceous materials, such as silica. A preferred silica is a precipitated amorphous hydrated silica, such as Sorbosil AC-35, marketed by Crosfield Chemicals, or Zeodent 115 from Huber Company but other abrasives may also be employed, including hydroxyapatite, sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, calcium carbonate, sodium bicarbonate, alumina trihydrate, aluminum silicate, calcined alumina and bentonite.

The concentration of abrasive in the potassium salt desensitizing component composition of the present invention will normally be in the range of 2 to about 40% by weight and preferably 5 to 25% by weight.

Other ingredients which may be incorporated in the potassium salt desensitizing component of the present invention, include pigment, sweetener, flavor and preservative. In white toothpaste formulations, the pigment will be titanium dioxide, rutile, and the proportion thereof will normally be in the range of 0.5 to 4% by weight, preferably 0.75 to 2.0% by weight. The sweetener content will normally be that of an artificial or synthetic sweetener and the normal proportion thereof present will be in the range of 0.1 to 1% by weight, preferably 0.3 to 0.5% by weight. The flavor content, which is preferably of a mixed peppermint/menthol flavor, will usually be in the range of 0.5 to 2% by weight, preferably 0.6 to 1.5% by weight. F.D. & C Grade dyes may be used in appropriate amounts to provide desired colors. The contents of other components or adjuvants of the desensitizing potassium salt containing dentifrice will normally not exceed 10% by weight, often will be less than 5% by weight, and can be as low as 0%.

To prepare the desensitizing potassium salt dentifrice component of the present invention, the humectant and thickening agent are dispersed in a conventional mixer until the mixture becomes a slurry which is smooth in appearance. Sweetener, color ingredients and non-ionic surfactant (such as Pluronic®) are then added to this mixture. Water is then added and this mixture may be heated to 100–110° F. and mixed for 10 to 30 minutes producing a homogeneous gel phase. The potassium salt desensitizing agent and alkaline agent are then added and mixed for 20 minutes or until completely dissolved. The mixture is then transferred to a vacuum mixer. The abrasive and inorganic thickener is added and mixed for 10 to 30 minutes at high speed under a vacuum in the range of 5 to 100 millimeter of mercury pressure, preferably 5 to 50 mm Hg, providing a homogenous mixture. The surfactant and flavor are then added to the paste which is followed by mixing another 5 to 20 minutes under vacuum of 5 to 50 mm Hg. The resultant product is a stable desensitizing dentifrice of a texture like that of conventional toothpastes or gels and of satisfactory flavor.

The tin salt containing dentifrice component of the present invention is generally comprised of about 0.1 to about 4.0% by weight of the tin salt. In the preparation of dentifrices containing tin salts such as $SnF_2$, the dentifrice contains about 0.30 to about 1.5% by weight $SnF_2$ and preferably 0.4 to 1.3% by weight. Additional stannous salts such as stannous chloride may also be added to improve the stability of the stannous fluoride salts in the range of 0.5 to 5%. The remainder of the tin salt dentifrice component is comprised of vehicle ingredients such as water, humectant, thickener, abrasive, flavor and surfactant generally similar to the materials used for the preparation of the potassium salt dentifrice vehicle.

The water and humectant comprise the liquid portion of the tin salt dentifrice component. The humectant will preferably be glycerin, but other humectants such as sorbitol and polyethylene glycol may also be employed. The humectant content is generally in the range of about 10% to about 50% by weight and preferably about 30 to about 50% by weight. The water content is in the range of about 10 to about 40% by weight and preferably 15 to 30% by weight.

An inorganic thickener may be incorporated in the tin salt dentifrice component at a concentration of about 0.5 to about 10% by weight and preferably about 1 to about 5% by weight. Organic thickeners of natural and synthetic gums of the same type used to prepare the potassium salt dentifrice component may also be incorporated at a concentration of about 0.1 to about 3% by weight and preferably about 0.2 to about 2% by weight.

A surfactant of the same type as used in the potassium salt dentifrice component is present at a concentration of about 0.5 to about 5.0% by weight and preferably about 0.75 to about 2.0% by weight.

Preferred abrasives are siliceous materials, such as silica, and preferably a precipitated amorphous hydrated silica, and preferably a precipitated amorphous hydrated silica, such as Zeodent 115, available from Huber Corporation. The abrasive is generally present in the at a concentration of bout 10 to about 40% by weight and preferably about 15 to about 30% by weight.

Also included in the tin salt dentifrice component of the present invention is an effective flavoring amount of a flavor compatible and stable with the tin salt. The flavor ingredient constitutes about 0.05 to about 1% by weight and preferably about 0.1 to about 0.5% by weight of the gel composition. Suitable flavoring constituents are flavoring oils, e.g. oils of spearmint, peppermint, wintergreen, clove, methyl salicylate and menthol.

Although a stannous salt such as $SnF_2$ is preferred for use in the practice of the invention, stannous salts other than $SnF_2$ may be used in the practice of the present invention. Examples of these other stannous salts include stannous chloride, stannous phosphate, stannous citrate and stannous gluconate. These salts may also be used in combination with the stannous fluoride salt.

An oxyethylated hydrogenated castor oil is advantageously included in both dentifrice components at a concentration of about 6% to about 8% by weight to reduce the astringency of the composition and render it more palatable to the user. Oxyethylated hydrogenated castor oil is a commercially available composition and is prepared by reacting for example about 40 to about 60 moles of ethylene oxide with one mole of hydrogenated castor oil. These compositions are available commercially under the trademark Cremophor available from Badische-Anilin-und Sodafabrick, Federal Republic of Germany.

A procedure preferred for the preparation of the tin salt dentifrice component is the preparation of a stannous salt premix as disclosed in U.S. Pat. No. 5,487,906, the disclosure of which is incorporated herein by reference, wherein the stannous salt is first dissolved in an aqueous solution of citric acid and its alkali citrate salts heated to about 110 to 120° F. The stannous salt premix solution prepared in this manner is then added to the tin salt dentifrice vehicle ingredients.

The vehicle ingredients include humectants such as glycerin and polyethylene glycol, having a molecular weight range of about which 200–8000, is prepared in a separate vessel. Organic thickening agents, sweetener and coloring agent are dispersed in this mixture. A polypropylene oxide such as a Pluronic® compound is then dispersed in this mixture. The aqueous stannous salt premix solution is then added and mixed for an additional twenty minutes. After this period, melted oxyethylated hydrogenated castor oil is added. The mixture is transferred to a vacuum mixer. Abrasive is then added and mixed for 10 to 30 minutes at high speed under a vacuum in the range of 5 to 100 millimeter of mercury pressure, preferably 5 to 50 mm Hg, providing a homogenous paste. The surfactant and flavor are then added to the paste which is followed by mixing another 10 to 20 minutes under vacuum of 5 to 50 mm Hg. The resultant product is a stable desensitizing dentifrice of a texture like that of normal toothpastes or gels and of satisfactory flavor.

Any convenient means for effecting the separation of the desensitizing potassium salt containing dentifrice component from the stannous salt dentifrice component during storage and before use can be utilized. For example, segregated tin salt containing dentifrice component and a desensitizing potassium salt containing dentifrice component are housed in a common container such as a collapsible tube and are separated from one another by a barrier, such as a wall integrally formed with the container which prevents mixing prior to the compositions being dispensed. The dental components of the present invention are then dispensed simultaneously as two ribbons when the tube is collapsed by hand pressure. Alternatively, the tin salt containing dentifrice component and a desensitizing potassium salt containing dentifrice component can be housed in separate containers from which the respective phases are dispensed sequentially and combined for admixture immediately prior to use.

The following examples are further illustrative of the present invention, but it is understood that the invention is not limited thereto. All amounts and proportions referred to herein and the appended claims are by weight.

EXAMPLE 1

A $SnF_2$ dentifrice useful as a component of the two component tooth desensitizing composition of the present invention was prepared with the following ingredients:

$SnF_2$ Dentifrice

| Ingredient | Concentration (wt %) |
| --- | --- |
| Water | 25.600 |
| Citric Acid | 0.531 |
| Sodium Citrate | 2.657 |
| Stannous Fluoride | 0.908 |
| Stannous Chloride | 0.600 |
| Glycerin | 33.704 |
| Xanthan Gum | 0.500 |
| Sodium Carboxymethylcellulose | 0.700 |
| Sodium Saccharin | 0.400 |

-continued

SnF₂ Dentifrice

| Ingredient | Concentration (wt %) |
|---|---|
| Tetrasodium Pyrophosphate | 0.500 |
| Pluronic ® | 2.000 |
| 1% dye solution | 0.300 |
| PBG 40 Castor Oil* | 6.000 |
| Zeodent 115 | 20.000 |
| Zeodent 165 | 3.000 |
| Flavor | 1.100 |
| Sodium Lauryl Sulfate | 1.500 |

*Oxyethylated hydrogenated castor oil

A potassium nitrate paste useful as a component of the two component dentifrice of the present invention was prepared with varying concentrations of sodium hydroxide, having the compositions identified below as Compositions 1, 2 and 3. For purposes of comparison, a dentifrice composition designated "Composition C", which was prepared without NaOH and the ingredients of Composition C are also listed below.

KNO3 DENTIFRICE COMPONENTS (KNO3 PASTE)

| COMPOSITION Ingredients | 1 | 2 | 3 | C |
|---|---|---|---|---|
| | Weight % | | | |
| Glycerin | 11 | 11 | 11 | 11 |
| Zeodent 115 | 22 | 22 | 22 | 22 |
| Deionized water | 40.2 | 41.2 | 42.2 | 43.2 |
| PEG-40 Castor Oil | 6 | 6 | 6 | 6 |
| Potassium nitrate | 10 | 10 | 10 | 10 |
| Polyethylene glycol 600 | 3 | 3 | 3 | 3 |
| Sodium lauryl sulfate | 1.5 | 1.5 | 1.5 | 1.5 |
| Carboxymethyl cellulose | 0.8 | 0.8 | 0.8 | 0.8 |
| Viscarin TP-206 (Carrageenan) | 0.8 | 0.8 | 0.8 | 0.8 |
| Titanium Dioxide | 0.2 | 0.2 | 0.2 | 0.2 |
| Sodium saccharin | 0.4 | 0.4 | 0.4 | 0.4 |
| NaOH (50% by wt) | 1.0 | 2.0 | 3.0 | 0.0 |
| Flavor | 1.1 | 1.1 | 1.1 | 1.1 |
| Total | 100 | 100 | 100 | 100 |

The glycerin, polyethylene glycol and organic thickeners were dispersed in a conventional mixer until the mixture became a slurry, which was smooth in appearance. Color and sweetener were dispersed in this slurry before the addition of water. This mixture was heated to a maximum of 140° F. and mixed for 20 to 30 minutes producing a homogeneous gel phase. Sodium hydroxide and potassium nitrate were then dispersed in this gel phase. This mixture was added to a vacuum mixer. The Zeodent 115 was then added and mixed for 10 to 30 minutes at high speed under a vacuum of about 50 mm Hg, providing a homogenous mixture. The sodium lauryl sulfate and flavor were then added to the paste which was followed by mixing another 20 minutes under vacuum of 50 mm Hg. The resultant product was a toothpaste with a satisfactory flavor.

The $SnF_2$ dentifrice and $KNO_3$ dentifrice components prepared above were both of extrudable consistency. After several days of storage, separate ribbons of the gel and paste compositions which when combined formed a treatment composition were extruded simultaneously at a 50:50 volume ratio onto dentin squares (4.25 mm×4.25 mm×800 mm) cut from extracted human molars which had been etched with 6% citric acid for 2 minutes to remove the smear layer. The so-prepared squares were treated with the gel/paste mixture 3 times/day for 5 days. Treatment involved brushing the dentin squares for 45 seconds with the treatment composition and then placed in a 10 ml rinse bath to remove excess treatment composition. The rinsed squares were stored in an artificial saliva solution (100 ml) between brushings. A stir bar was used to mix the solutions. After the last brushing, the squares were put into a deionized water solution to rinse off the artificial saliva. The squares were then dried and submitted for Electron Spectroscopy for Chemical Analysis (ESCA) and Scanning Electron Microscopic Analysis (SEM). The results of the ESCA analysis is recorded in Table I below.

TABLE I

| | ESCA RESULTS Atomic Percent | | | | | | | |
|---|---|---|---|---|---|---|---|---|
| $KNO_3$ Paste Used in Treatment | C | O | N | Ca | P | Sn | Si | F |
| 1 | 30.51 | 45.15 | 5.06 | 5.81 | 4.42 | 0.97 | 7.84 | 0.23 |
| 2 | 33.69 | 42.98 | 6.90 | 2.90 | 2.11 | 0.54 | 10.72 | 0.16 |
| 3 | 35.97 | 40.83 | 8.45 | 2.33 | 1.65 | 0.34 | 10.28 | 0.15 |
| C | 37.89 | 39.22 | 8.65 | 3.99 | 3.07 | 0.77 | 6.20 | 0.23 |

The results recorded in Table I indicate that although increasing amounts of sodium hydroxide in the treatment composition did not increase the amount of tin deposited on the dentin surface, substantial increases in the amount of silica were noted.

Figure 2:
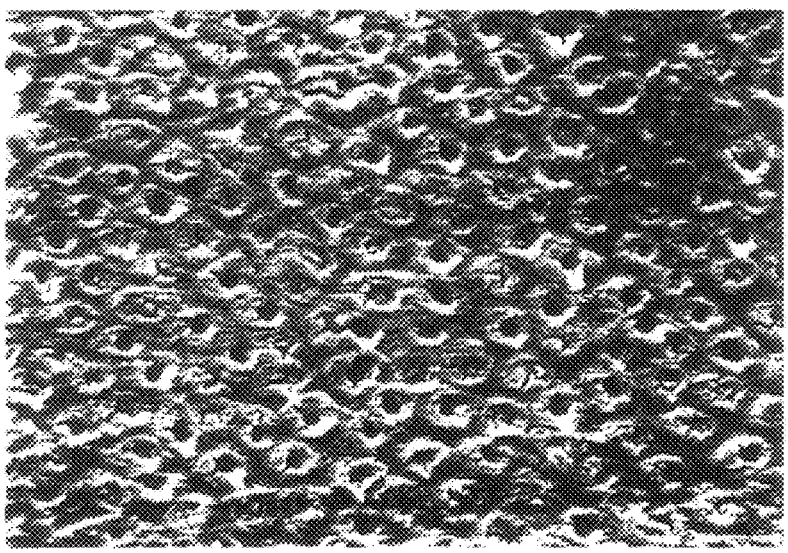
FIG. 2 is a SEM (2,000×magnification) of a dentin disk surface treated in a comparative manner with a dual component dentifrice containing both tin and potassium salts in which an alkaline agent was not present.

The SEM photomicrograph FIG. 1 shows the results of the dentinal surfaces treated with a mixture of the $SnF_2$ dentifrice and $KNO_3$ dentifrice number three which when combined contained 1.5% by weight sodium hydroxide. Examination of this photomicrograph indicates that dentinal tubule obtruation was substantially complete and left more debris on the dentin surfaces than a comparative treatment composition in which NaOH was absent, namely Composition C, as can be observed from the SEM photomicrograph of FIG. 2.

Figure 3:
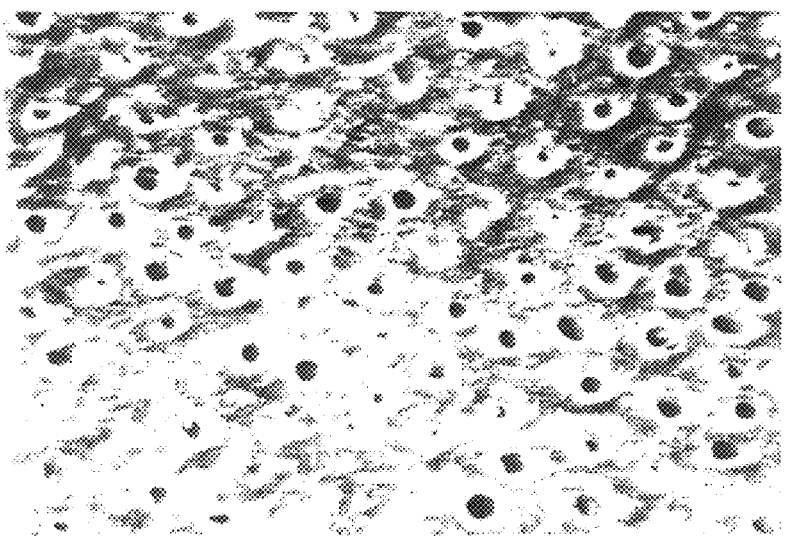
FIG. 3 is a SEM (2,000×magnification) of a dentin disk surface treated with a comparative manner with a conventional single component KNO3/NaF dentifrice.

For purposes of further comparison, the procedure of the example was repeated except a single component dentifrice containing 5% by weight potassium nitrate and 0.243% sodium fluoride was evaluated for dentinal tubinal obtruation. FIG. 3 is a SEM photomicrograph of a dentin surface treated in this comparative manner. As can be observed from an examination of the photomicrograph dentinal tubule obturation, was found to be minimal.

To determine if the deposits formed when NaOH was present in the treatment composition reduce flow through dentinal tubules, dentin disks sections were cut from extracted human molars to a thickness of 800 mm. The smear layer of the disks was removed with 6% citric acid over a 2 minute time period. The baseline flow was measured for each of the prepared disks using an apparatus similar to that described in J. Dent. Res. (1997) 56, p. 1161–64. Fluid flow was measured through each disk with 70 cm of hydrostatic pressure. Disks were treated 3 times/day for 5 days. Between brushings a continuous stream of artificial saliva solution was flowed over the disks. The disks were stored in 5 ml of distilled deionized water upon completion of the treatment which was then followed by a measurement of flow rates through the treated disks. The disks were dried after the final flow measurements and the surface was analyzed using ESCA. Each treatment was tested with three disk samples.

For purposes of further comparison, the procedure was repeated except a commercial desensitizing toothpaste designated "$C_1$" containing 5% by weight $KNO_3$ and 0.243% NaF was evaluated. As a control, a phosphate buffer solution (0.2 mM Ca, 0.2 mM phosphate, 150 mM NaCl, pH=7) was used.

The results of the flow occlusion tests are shown in Table II. In Table II, Flow After Treatment as % Baseline flow= (flow after treatment)/(flow before treatment) times 100. Values less than 100 indicate the treatment reduced the flow rate from baseline. This is indicative of occlusion.

TABLE II

FLOW OCCLUSION RESULTS

| Treatment Composition | Baseline Flow mg/15 minutes | Flow After Treatment (mg/15 min.) | Flow After Treatment as a % of Baseline Flow |
|---|---|---|---|
| 2 | 231.84 | 190.7 | 82.2 |
| 3 | 231.04 | 153.0 | 66.2 |
| C | 227.38 | 201.0 | 88.4 |
| $C_1$ | 223.28 | 238.5 | 106.8 |
| $C_2$ | 225.94 | 283.9 | 125.7 |

The data recorded in Table II indicate that the presence of sodium hydroxide in the treatment composition significantly increased flow occlusion. The treatment composition with the highest level, 1.5%, of sodium hydroxide (Composition 3) was the composition most effective in promoting flow occlusion, that is, flow was 66.2% of the base line flow.

The ESCA results recorded in Table III follow the same trends as the previous reported flow occlusion test. The percentage of tin on the surface is decreased with the addition of hydroxide but the percentage of silicon increases with the amount of sodium hydroxide in the formula.

TABLE III

ESCA RESULTS FROM FLOW OCCLUSION STUDY
Atomic Percent

| Treatment | C | O | N | Ca | P | Sn | Si | F |
|---|---|---|---|---|---|---|---|---|
| 2 | 43.24 | 36.17 | 9.08 | 3.98 | 2.90 | 0.35 | 4.24 | 0.05 |
| 3 | 40.94 | 38.36 | 8.50 | 2.94 | 2.10 | 0.25 | 6.90 | 0.02 |
| C | 39.77 | 39.18 | 7.38 | 6.08 | 4.45 | 0.77 | 2.23 | 0.15 |
| $C_1$ | 55.51 | 27.28 | 12.79 | 2.06 | 1.61 | — | 0.75 | — |
| $C_2$ | 56.52 | 25.64 | 13.55 | 1.84 | 1.37 | 0.04 | 1.04 | 0.09 |

What is claimed is:

1. A composition for treating dentinal hypersensitivity by applying to teeth requiring relief from hypersensitivity an improved desensitizing two component dental composition which eliminates or reduces the discomfort and pain associated with dentinal hypersensitivity which composition comprises a first aqueous dentifrice component containing a potassium salt desensitizing agent and about 0.5 to about 15% by weight of an alkali metal compound to maintain the pH of the component in the range of about 8 to about 11, a second aqueous dentifrice component containing a desensitizing stannous salt and in which the alkali metal compound is absent, the first and second components being maintained separate from each other until dispensed for application to teeth requiring relief from dentine hypersensitivity, whereby heightened desensitization is observed.

2. The composition of claim 1 wherein the potassium salt is potassium nitrate.

3. The composition of claim 1 wherein the stannous salt is stannous fluoride.

4. The composition of claim 1 wherein the potassium salt containing dentifrice component is an aqueous dentifrice having a pH of about 8 to about 11.

5. The composition of claim 1 wherein the alkali metal compound is sodium hydroxide.

6. The composition of claim 1 wherein the alkali metal compound is present in the potassium salt containing dentifrice component at a concentration of about 1 to about 8% by weight.

7. The composition of claim 1 wherein the alkali compound is present in the potassium salt containing component at a concentration of about 1 to about 5% by weight.

8. A method for treating dentinal hypersensitivity by applying to teeth requiring relief from dentine hypersensitivity an improved desensitizing two component dental composition for eliminating or reducing the discomfort and pain associated with dentinal hypersensitivity which comprises preparing the improved composition which is comprised of (1) a first aqueous dentifrice component containing a potassium salt desensitizing agent and about 0.5 to about 15% by weight of an alkali metal compound to maintain the pH of the component in the range of about 8 to about 11 and (2) a second aqueous dentifrice component containing a desensitizing stannous salt and in which the alkali metal compound is absent, separately housing the first and second components, dispensing the first and second components simultaneously, combining the dispensed components for application to teeth requiring relief from dentine hypersensitivity and thereafter applying the combined components to the teeth whereby heightened desensitization is observed.

9. The method of claim 8 wherein the potassium salt is potassium nitrate.

10. The method of claim 8 wherein the stannous salt is stannous fluoride.

11. The method of claim 8 wherein the potassium salt containing dentifrice component is an aqueous dentifrice having a pH of about 8 to about 11.

12. The method of claim 8 wherein the alkali metal compound is sodium hydroxide.

13. The method of claim 8 wherein the alkali metal compound is present in the potassium salt containing dentifrice component at a concentration of about 1 to about 8% by weight.

14. The method of claim 8 wherein the alkali compound is present in the potassium slat containing component at a concentration of about 1 to about 5% by weight.

15. The method of claim 8 wherein the first and second components are housed in a common container and are separated from one another by a wall integrally formed with the container which prevents mixing of the components prior to being dispensed.

* * * * *